US00RE40559E

(19) United States
(12) Reissued Patent
Lev

(10) Patent Number: US RE40,559 E
(45) **Date of Reissued Patent: *Oct. 28, 2008**

(54) RADIATING DEVICE FOR HYPERTHERMIA

(75) Inventor: Avigdor Lev, Amsterdam (NL)

(73) Assignee: Medical Enterprises, Ltd., Bridgetown (BB)

( * ) Notice: This patent is subject to a terminal disclaimer.

(21) Appl. No.: 09/923,279

(22) PCT Filed: May 3, 1994

(86) PCT No.: PCT/IT92/00142

§ 371 (c)(1),
(2), (4) Date: May 3, 1994

(87) PCT Pub. No.: WO93/09724

PCT Pub. Date: May 27, 1993

(65) Prior Publication Data

US 2002/0077625 A1 Jun. 20, 2002

Related U.S. Patent Documents

Reissue of:
(64) Patent No.: 5,431,648
Issued: Jul. 11, 1995
Appl. No.: 08/232,190
Filed: May 3, 1994

U.S. Applications:
(63) Continuation of application No. 08/889,825, filed on Jul. 8, 1997, now Pat. No. Re. 37,315.

(30) Foreign Application Priority Data

Nov. 11, 1991 (IT) ..... MI91A2993

(51) Int. Cl.
*A61B 18/18* (2006.01)
*A61N 5/04* (2006.01)
*A61N 5/02* (2006.01)
*A61F 7/12* (2006.01)

(52) U.S. Cl. ..... 606/27; 606/42; 607/101; 607/105; 604/96.01

(58) Field of Classification Search ..... 606/27–31, 606/41, 42, 45–50; 607/101, 102, 104, 105; 600/549
See application file for complete search history.

(56) References Cited

U.S. PATENT DOCUMENTS

| | | | | | |
|---|---|---|---|---|---|
| 4,154,246 | A | * | 5/1979 | LeVeen | |
| 4,375,220 | A | * | 3/1983 | Matuias | 607/102 |
| 4,676,258 | A | | 6/1987 | Inokuchi et al. | |
| 4,924,863 | A | * | 5/1990 | Sterzer | |
| 4,967,765 | A | * | 11/1990 | Turner | |

(Continued)

FOREIGN PATENT DOCUMENTS

| | | | | |
|---|---|---|---|---|
| EP | 0370890 | * | 5/1990 | |
| FR | 2679456 | * | 1/1993 | 607/101 |
| GB | 2045620 | * | 5/1980 | |
| JP | 60-119962 | | 6/1985 | |
| JP | 62-94152 | | 4/1987 | |
| WO | WO8911311 | * | 11/1989 | |
| WO | WO9003152 | * | 5/1990 | |

*Primary Examiner*—Michael Peffley
(74) *Attorney, Agent, or Firm*—Finnegan, Henderson, Farabow, Garrett & Dunner, LLP

(57) ABSTRACT

A flexible three-paths catheter provided with a balloon carries a sealingly sheathed radiofrequency radiating antenna, together with the shielded power supply cable and with some thermocouples, within a plastic lining surrounded by a flow of liquid; a second path carries the power supply cables of some outer thermocouples, flooded by the reverse liquid flow, while the third path allows a fluid to flow through for inflating the balloon.

Introduction of the catheter into a hollow organ makes it possible to perform hyperthermal therapy of tumors by means of radiation.

11 Claims, 4 Drawing Sheets

U.S. PATENT DOCUMENTS 5,000,734 A * 3/1991 Boussignac et al. ..... 604/96
5,007,437 A * 4/1991 Sterzer
5,090,958 A * 2/1992 Sahota ..... 604/96 X
5,103,804 A * 4/1992 Abele et al. ..... 607/105 X
5,168,880 A * 12/1992 Sogawa et al. ..... 607/102
5,191,883 A * 3/1993 Lennox et al. ..... 606/27 X

* cited by examiner

RADIATING DEVICE FOR HYPERTHERMIA

Matter enclosed in heavy brackets [ ] appears in the original patent but forms no part of this reissue specification; matter printed in italics indicates the additions made by reissue.

*CROSS REFERENCE TO RELATED APPLICATIONS*

*This application is a continuation of reissue application No. 08/889,825, filed on Jul. 8, 1997, now U.S. Pat. No. RE37,315, which is a reissue of U.S. Pat. No. 5,431,648 based on application No. 08/232,190, filed May 3, 1994.*

BACKGROUND OF THE INVENTION

This invention concerns a radiating device for hyperthermia and, more particularly, a radiofrequency radiating device, for hyperthermal treatment of tumors of the bladder.

Devices for hyperthermal treatment of various human body illnesses are already known, and they use heating liquids, light radiation, radiofrequency antennas, thermistors, and so on.

U.S. Pat. No. 4,776,334 describes a catheter for treating tumors by inserting within the tumor to be treated a radiofrequency device provided with temperature sensors.

French patent application 2600205 concerns an apparatus for light irradiation of a cavity with the help of an inflatable balloon and of light sensors.

In U.S. Pat. No. 4,154,246 there is described a radiofrequency resonating circuit which is introduced in natural cavities of the body or directly inserted into the tumoral mass.

German patent application No. 2,848,636 claims usage of a heated liquid which is circulated in a closed loop by means of a pump within a body cavity, wherein the liquid temperature is controlled by an external thermostat EP-A-0 370 890 discloses a radiating [urathral] *urethral* device for hyperthermia including a catheter provided with an inflatable balloon and adapted to receive one or more liquid flows passing therethrough, a radiofrequency radiating antenna, and one or more thermocouples, the radiating antenna being submerged within one said liquid flow coming back from the closed terminal end of the antenna. The radiating device comprises in addition a separate rectal control means.

GB-A-2 045 620 relates to an applicator for hyperthermia comprising a rectal radiating probe and a spaced apart transurethral catheter including a temperature sensing means and an inflatable balloon. U.S. Pat. No. 4,957,765 discloses a transurethral radiating applicator for hyperthermia including a multi-tubes balloon type catheter comprising closed and [cubes] *end tubes* respectively surrounding a helical coil antenna and a temperature sensor, as well as a passive drainage tube for urine.

It is an object of this invention to provide a device for hyperthermal treatment of tumors within natural cavities of the human body, which gathers the advantages of the known devices while being free from their drawbacks.

SUMMARY OF THE INVENTION

The device according to this invention substantially comprises a flexible triple path catheter carrying a radiofrequency radiating antenna, sealingly sheathed together with the shielded cable providing power supply and with several thermocouples within a plastic casing and surrounded by a flow of liquid; a second path carries the power supply cables for several outer thermocouples, which are flooded by return flow of said liquid, and a third path allowing a fluid to flow through in order to inflate a balloon located near the catheter distal end, once the latter has been introduced into the cavity to be treated.

This invention will be described more particularly in the following based on a specific embodiment thereof reported herein for exemplary and non limiting purposes, as well as on the attached schematic drawings. In connection with the above it should be pointed out that in said drawings the parts shown are not to scale and the mutual dimensions are out of proportion, the members having in fact a very thin cross-section.

DESCRIPTION OF THE PREFERRED EMBODIMENTS

Figure 1:
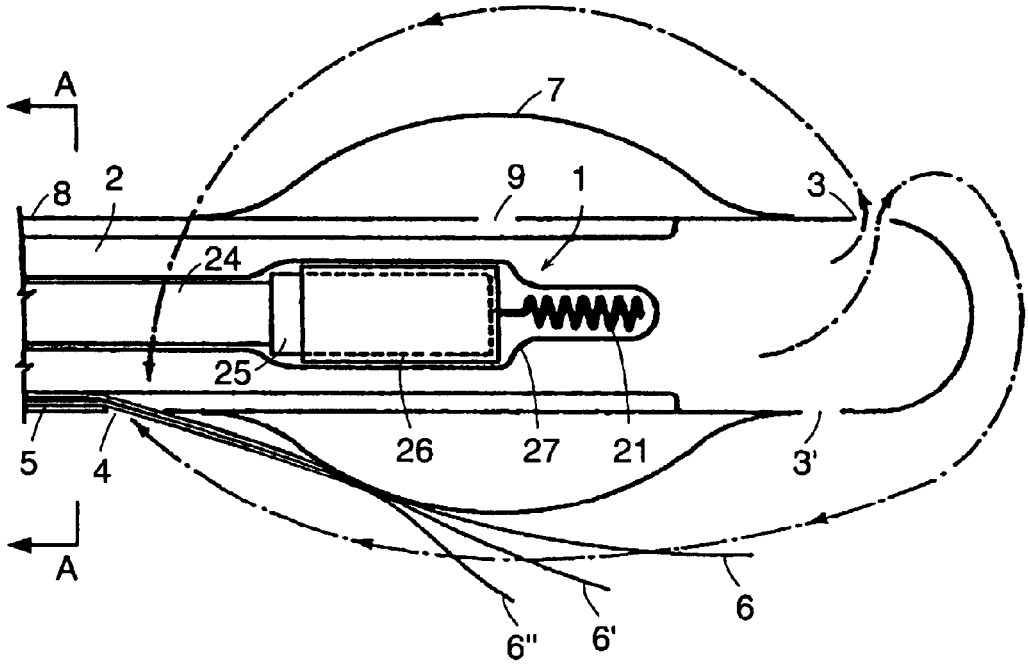
FIG. 1 shows schematically, in an enlarged scale, the distal end of the device according to this invention, which has to be introduced into a natural cavity of the human body.

The device according to this invention has a shape and consistency of a flexible catheter whose distal end, as it is shown in FIG. 1, encloses therewithin an antenna 1 surrounded by a flow of liquid 2 which is introduced into the bladder through an opening 3 and, after being freely circulated within said bladder, is again sucked into the catheter through an opening 4. Said opening 4 is in communication with a second way or catheter side channel 5 housing the leads of several thermocouples, like for instance 6, 6', 6" adapted to be deflected outwards by inflating a balloon 7 in which a gaseous fluid or a liquid is made to flow through a third path or side channel 8 and through an end opening 9.

Figure 3:
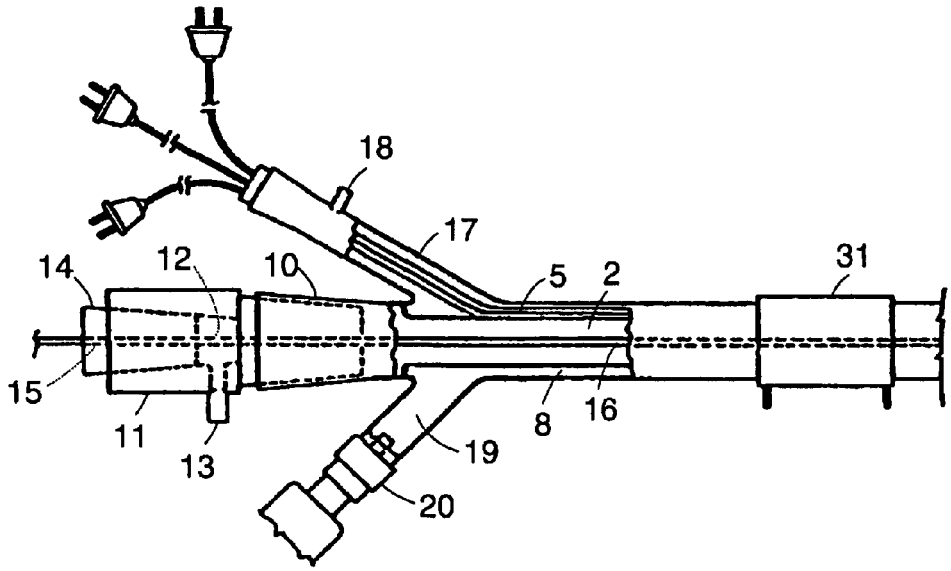
FIG. 3 is a schematic of the proximal end of the device according to this invention, opposite to the distal end shown in FIG. 1.

The catheter opposite (proximal) end (FIG. 3) whose tip is shown in FIG. 1, has three diverging inlets corresponding to the three paths or channels 2, 5, 8 of said catheter. Within center inlet 10 there is inserted with a pressure fit a plug 11 provided with a center through passage and with a side branch 13; in center passage 12 of plug 11 there is in turn pressure fitted a second plug 14 which is provided as well with a center opening 15. Shielded cable 16 supplying power to antenna 1 runs through the center passages 12 and 15 of said two coaxially arranged plugs, while side branch 13 is provided as an inlet and an outlet of a conditioning fluid flowing along channel 2. Thermocouple power supply cables 6, 6', 6" are laid through said entrance 17 provided with a branch 18, and they run along side path or channel 5 having said conditioning liquid flowing in a reverse direction therethrough, said liquid entering and exiting in turn through said branch 18. The other side entrance 19 is provided with a one-way valve 20 for introducing the fluid that, flowing along second side channel 8, is used to inflate balloon 7.

Slightly downstream from said three entrances 10, 17, 19 there is provided, in a sleeve-like fashion and in intimate contact around the catheter body, a heat exchanger 31, operated in a known fashion from outside, and used to cool or to heat said conditioning liquid flowing through central channel 2 and coming back through side channel 5, or viceversa.

Figure 2:
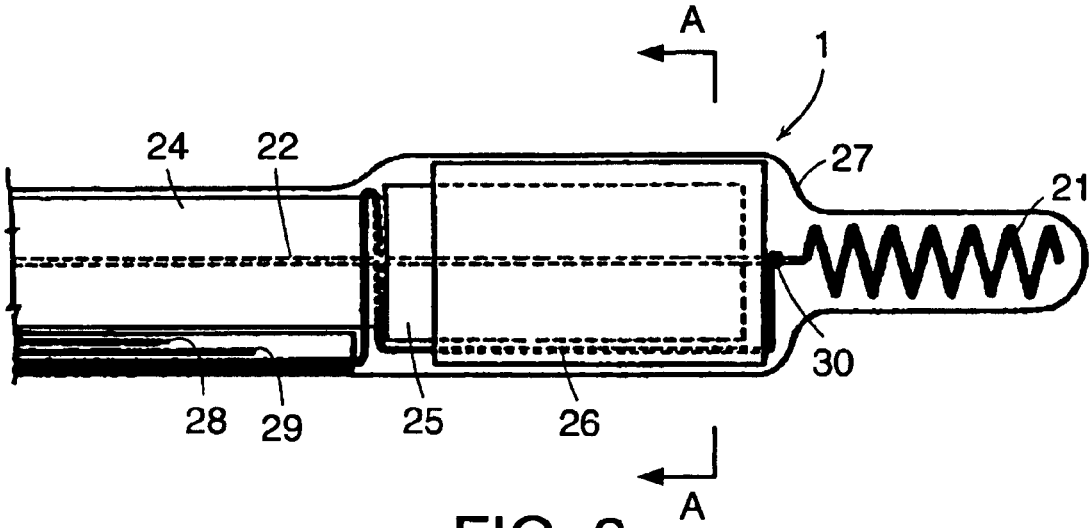
FIG. 2 is a schematic of some structural details of a radiofrequency antenna shown in general within the device of FIG. 1.
Figure 2A:
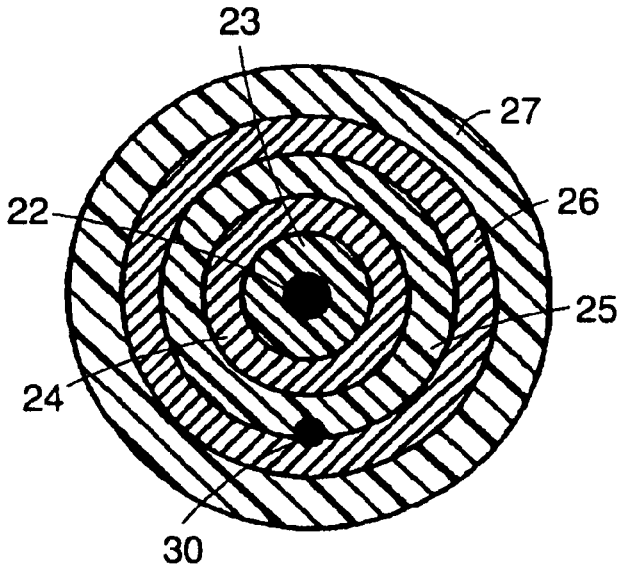
FIG. 2A shows a schematic enlarged cross-section of the radiating antenna, taken along line A—A of FIG. 2.

Referring now to FIGS. 2 and 2A, radiating antenna 1 will be described more in detail; the useful radiating portion of linear dipole antenna 1 comprises a terminal coil-shaped segment 21 of central conductor 22 which, immediately upstream from coil 21 is tightly surrounded, in sequence, by a first plastic inner sleeve 23, by a metal braiding 24, by a second intermediate plastic sleeve 25, by a metal cylinder 26 electrically connected with shield 24, and eventually by an outer plastic sleeve 27.

Immediately beneath sleeve 27 there is provided the power supply cables for several thermocouples located in a way suitable to detect the operating temperatures in predetermined positions of the antenna and of the power supply cable thereof. For instance, a first thermocouple 28 may be located in the position of the stretch of catheter which will be located at the prostatic urethra when the catheter with its antenna are inserted within the bladder; a second thermocouple 29 slightly upstream from antenna 1, at the bladder neck, while a third thermocouple 30 is located close to central conductor 22, between metal cylinder 26 and end coil 21, after having been wrapped with one or more coils around shield 24 immediately upstream from intermediate sleeve 25 and metal cylinder 26, and a second time, with a larger number of coils, around the stretch of central lead 22 projecting out of metal cylinder 26 before winding up to form end coil 21, the stretch of thermocouple 30 power supply cable connecting said two points being inserted with intimate contact between intermediate sleeve 25 and metal cylinder 26.

In any case, the end stretches of the power supply cables, immediately ahead of the thermocouples, are wrapped in a number of helical coils in order to increase the thermal capacity and the radiofrequency resistance of the ends which are designated to detect the temperature, while reducing to a minimum, or completely avoiding the dispersive thermal conduction along said cables.

Figure 1A:
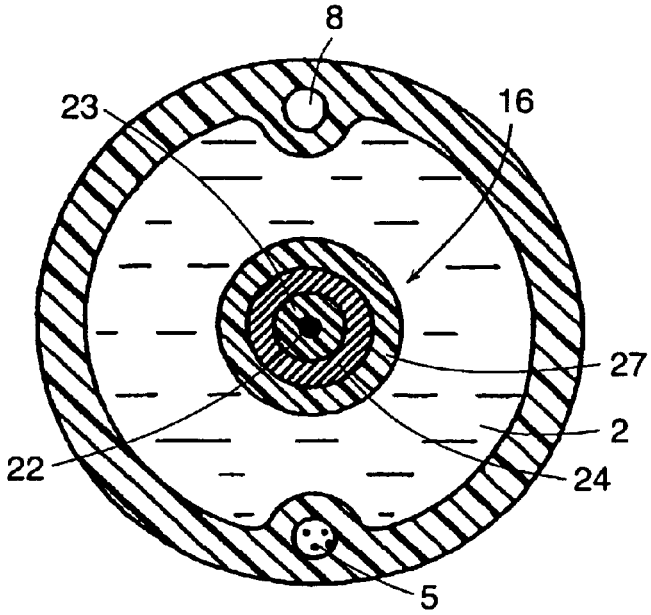
FIG. 1A shows an enlarged schematic cross-section of the device according to this invention, taken along line A—A of FIG. 1.

In FIG. 1A, which shows schematically a cross-section of the catheter according to this invention, taken in any position of the stretch going from heat exchanger 31 to intermediate sleeve 25, there is shown side channel 5 carrying the power supply cables of thermocouples 6, 6', 6" and side channel 8 for the flow of the fluid used to inflate balloon 7, both said channels 5 and 8 being managed within the thickness of the actual catheter whose inner bore 2 intended for the flow of the conditioning liquid carries, in a central position, shielded cable 16 comprised of central conductor 22, inner sleeve 23, shield 24 and outer sleeve 27, as well as inner thermocouples 28, 29 and 30 power supply cables (not shown).

FIG. 2A is a schematic cross-section of antenna 1, taken along line A—A of FIG. 2. The following are shown therein, starting from the center: conductor 22, inner sleeve 23, metal shield 24, an intermediate sleeve 25, a metal cylinder 26, and outer sleeve 27, as well as thermocouple 30 power supply conductor.

Figure 4:
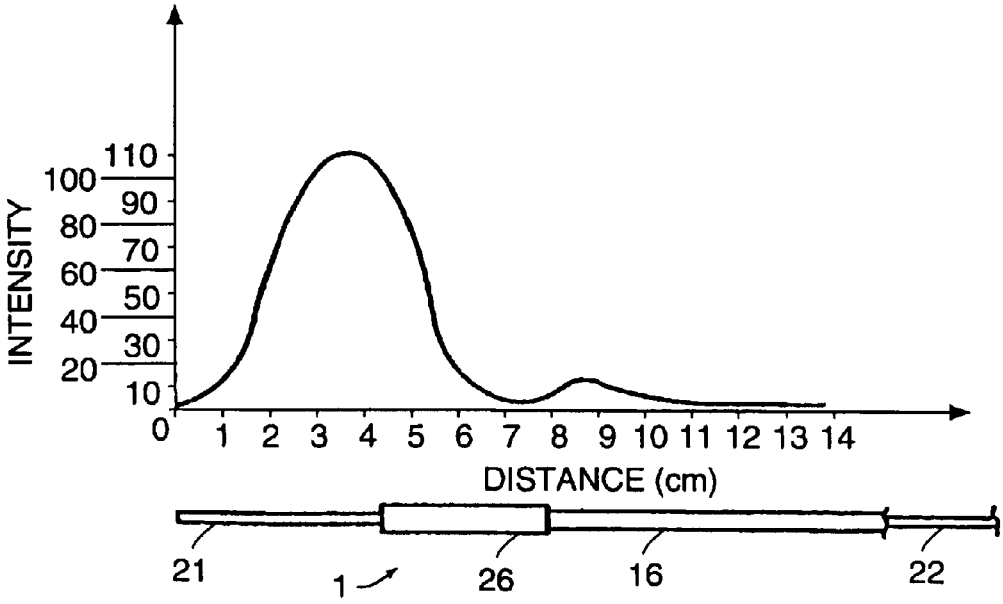
FIG. 4 is a plot of the intensity of the radiation generated by the radiating antenna of FIG. 2, along the longitudinal axis thereof.

FIG. 4 is a diagram showing the radiation intensity starting from the coil-shaped end 21 of antenna 1 towards shielded power supply cable 22, 16. As it is shown, intensity is a maximum when passing from radiating coil 21 to the stretch protected by metal cylinder 26, and it tends to nil at the position of shielded cable 16.

Figure 5:
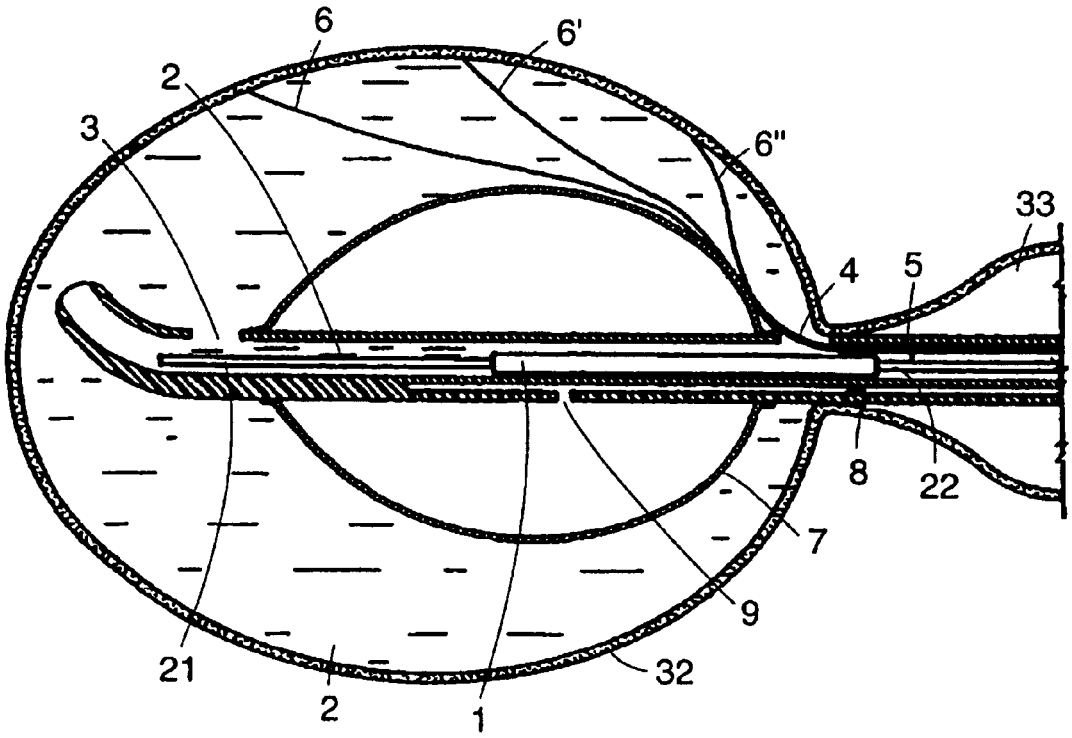
FIG. 5 shows schematically the distal end of the device of FIG. 1, as it is seen after having been introduced into a urinary bladder.

There is shown schematically in FIG. 5 the longitudinal section of the catheter provided with a radiating antenna according to this invention, once it has been introduced into the bladder, in an operative condition. The catheter, carrying the radiating antenna there-within, is introduced into bladder 32 through the urethra, in such a way that the rear end of protective metal cylinder 26 is located approximately at the bladder neck, in the transition area between [prostata] *prostrate* 33 and bladder 32, while simultaneously taking care that the catheter front end does not subject the bladder internal wall to any pressure. Once the catheter has been introduced into the bladder in such a way, one actuates the supply pump of conditioning liquid 2 preferably comprising a solution of a selective [citotoxicity] *cytotoxicity* substance, which is accordingly forced to circulate through the bladder coming out from opening 3 and going back through opening 4, or viceversa, along side channel 5 which carries the power supply cables of thermocouples 6, 6', 6" therewithin. The liquid forced circulation, provided by the variable flowrate supply pump, suitably combined with an outer balancing and degassing chamber, allows the volume of liquid within the bladder to be balanced at will, in such a way as to compensate the pathological or physiological urine production, while thoroughly ejecting the gases generated or unwillingly introduced in circulation, out of the bladder, in order to prevent irradiation non-uniformities which would otherwise be caused by coexistance of anisotropic media. Once bladder 32 has been completely filled with conditioning liquid 2, ballon 7 is inflated by introducing a fluid, which may be a gas but it is preferably a liquid, along side channel 8 and through the end opening 9 thereof; ballon 7 inflated as mentioned above, pushes then against outer thermocouples 6, 6', 6" power supply cables thereby moving said thermocouples into tangential engagement against bladder wall 32 in different positions, in order to detect the temperatures prevailing therein as caused by irradiation generated by antenna 1. The possibility of changing the location and the number of the outer thermocouples, enables the thermocouples to be positioned at will, on the bladder wall, or in any [case] *place* of the body organ to be treated, while being able to individually check the temperatures in the various locations. The inflated ballon 7 protects the bladder neck wall from an excess heat caused by the proximity of the radiating antenna, and in the meantime it prevents the catheter from being accidentally displaced or from coming out through the bladder neck.

The dimensions of antenna 1 are such that it may be freely positioned along the catheter while being obviously wholly contained within the human bladder to be treated, but in the meantime they must be suitable to generate a therapeutically active radiation, in order to reach the temperatures considered lethal for the cancer cells. Since the physical length of an antenna is related to the virtual electrical length thereof through an equation involving the impedance of said antenna, as well as the impedance deriving from the environment irradiated by the antenna, the antenna electrical length comes out to be inversely proportional to the irradiated medium conductivity. Accordingly, since the conductivity of an aqueous solution is for instance many times higher than the conductivity of air, when operating in an aqueous environment it is possible to use an antenna which is physically quite shorter than the length needed if it were necessary to operate in air.

The dipole according to this invention corresponds to a dipole of the quarter wave type and in the aqueous environment comprising the solution filled bladder, it makes it possible to operate at frequencies in the range of 900–1000 MHz; in particular, a frequency of 915 MHz has been chosen since very different frequencies would result in penetration, intensity, and other effects not always exactly predictable and controllable in the body tissues, since in general high frequencies have a low penetration power and therefore they do not provide the desired local heating, while lower frequencies, having a higher penetration power, may get deeper tissues involved and damaged.

On the other hand, radiations having different wavelengths might create a disturbance for radio and telephone communications, protected by constraints imposed by the legislations of the various countries.

In order to reduce to a minimum and possibly to nil the influence of the radiofrequency field of the thermocouples, as well as the various thermoelectric effects connatural with said thermocouples, the supply cable end stretches close to the thermocouples are wound into an helical shape whereby the temperature measured in the various sensing points is a reliable data, unaffected by said influences. The above structure construction prevents measuring errors due to conduction, it provides a reliable temperature indication, for instance exactly in the area of the dipole power supply position in the case of thermocouple 30, and it reduces in an extremely effective manner the thermocouple self-heating process due to radiofrequencies, also when there is an extremely high concentration of energy, whereby said structures are almost unaffected by the disturbances in the radiofrequency field.

Since the sizes, and in particular the cross-sections of the plural device components according to this invention must be extremely small, to suit the particular field of use desired for the device, the energy losses due for instance to self-heating of the antenna power supply cable are particularly high, for instance in the range of 20–40%. Since this undesirable self-heating, due to the Joule effect, might cause excessive heating of the urethral walls, and accordingly a discomfort for the patient subjected to treatment, or even damages to the tissues, the antenna cable, and the antenna itself are continuously cooled, while in operation, by using the conditioning liquid flow directed to the bladder and then withdrawn again therefrom, whereby a simultaneous control action is obtained, for controlling the temperature prevailing both in the liquid within the bladder and along the urethra. Temperature control is effected by variations of the conditioning liquid supply flow and of the cooling source temperature. In such a way it is possible both to increase the temperature and to withdraw heat.

In order to enable outer thermocouples 6, 6', 6" for detecting the bladder wall temperature to be safely deflected outwards when [ballonon] *balloon* 7 is inflated, the power supply cables thereof are reinforced along their whole length by inserting within the protecting sheath thereof a thin stainless steel wire providing them with the required rigidity and flexibility. The presence of said reinforcing wire provides as well [he] *the* thermocouple power supply cables with the mechanical strength necessary to bear the compressive and tensile stresses caused when the cables are inserted within side channel 5, and when thermocouples 6, 6', 6" are laid in the desired locations.

Figure 6:
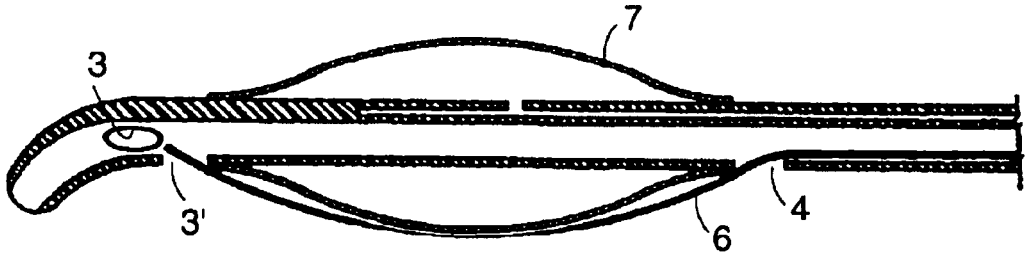
FIG. 6 shows schematically the structure at the distal end of the device shown in FIG. 1, when ready for introduction into the organ to be treated.

When the catheter, provided with all its components, is introduced into the urethral channel, all the way to the bladder, the ends of outer thermocouples 6, 6', 6" projecting upstream of balloon 7 through opening 4 are temporarily locked by inserting them, downstream of balloon 7, in one or more notches provided, as the case may be, in suitable positions according to the different body organ or the particular patient to be treated, close to the catheter end, as it is shown in FIG. 6. When balloon 7 is inflated it causes the thermocouple ends to come out from the notches and then to deflect outwards until the thermocouple tips come into engagement with the bladder wall. The particular outwards deflecting system of thermocouples 6, 6', 6" causes the ends of the respective power supply cables comprising the actual thermocouple, to tangentially engage the bladder wall, whereby no excessive concentrated pressures are generated. On the other hand, the tangential position taken by the thermocouple tips when contacting the bladder wall, makes it possible to measure the actual temperature of the wall position considered in that at the boundary between said wall and the liquid filling the bladder there is a thin liquid layer substantially stationary, which is not affected by the liquid circulation within the bladder, since it clings to the tissue because of a physical attraction, while the coil shape of the cable terminal stretches increases the thermal capacity of the thermocouple whose diameter, inclusive of the coils, is less than 0,7 mm whereby the thermocouple is completely submerged within the liquid stationary layer having a thickness of approximately 1 mm.

After the thermocouples have been deflected outwards within the bladder, it is still possible to modify their location by performing pushing and/or pulling actions on the reinforced power supply cables, as mentioned above, and possibly by rotating the catheter containing them. Control of the temperature detected on the bladder walls and/or within the circulating liquid mass, is obtained by changing the flowrate of said liquid from few cubic centimeters per minute to several tens of cubic centimeters per minute. The circulated fluid circulating system prevents permanence or formation and build-up of possible gas bubbles within the bladder or through the circuit, in that air or other gas bubbles having possibly formed or being already present, are entrained out by the continuous flow and exhausted to the outer environment in an appropriate position of the outer pumping circuit. In addition, the liquid circulation provided as above [presents] *prevents* the antenna and the environment thereof from overheating, therefore from causing undesirable reactions within the circulating liquid.

It is pointed out herein that all the antenna and thermocouple components contacted by the liquid circulating within the bladder are sealingly lined and insulated from the outer environment by a polytetrafluoroethylene layer whereby, after each usage and application they may be sterilized for subsequent further use.

We claim:

[1. A radiating device for urethral hyperthermia including a catheter provided at its distal end with an inflatable balloon (7) and adapted to receive multiple injected liquid flows (2,5, 8) passing therethrough, a radiofrequency radiating antenna (1) and multiple thermocouples (6,6',6"), the radiating antenna being submerged within said liquid flow, characterized in that said radiating antenna (1) is submerged within a liquid flow which proceeds through a central channel (2) surrounding said radiating antenna (1) towards the distal end of said catheter and passes from said catheter through a first opening (3) into the bladder to be treated, while flowing back into said catheter towards the proximal end thereof through a second separate opening (4) of a side channel (5) surrounding the power supply cables of said thermocouples (6,6',6"), the ends of said thermocouples (6,6',6") project out of said second opening (4), being thus deflected outwards into the bladder when said balloon (7) is inflated by injecting a fluid therein through a second side channel (8) and third opening (9), whereby the outwardly deflected ends of said thermocouples (6,6',6") come into tangential engagement with the bladder wall (32) irradiated by said antenna (1).]

*2. A radiating device for irradiating a cavity comprising:*

*a catheter;*

*an antenna, situated at a distal portion of the catheter, for irradiating the cavity;*

*a central channel adapted to provide a fluid to the cavity;*

*a side channel adapted to receive the fluid from the cavity;*

*at least one side branch, situated at a proximal portion of the catheter; and*

*at least one temperature sensing device, having an end, the end of the at least one temperature sensing device extending outward from the catheter after the catheter is inserted into the cavity;*

*wherein the end of the at least one temperature sensing device is adapted to detect a temperature of a wall of the cavity irradiated by the antenna.*

*3. The radiating device according to claim 2 wherein the at least one side branch provides an inlet for the fluid to enter the central channel.*

*4. The radiating device according to claim 2 wherein the at least one side branch provides an outlet for the fluid to exit from the side channel.*

*5. The radiating device according to claim 2 further comprising:*

*an inflatable balloon situated at the distal portion of the catheter;*

*a second side channel adapted to provide a fluid used to inflate the inflatable balloon; and*

*a one-way valve for introducing the fluid used to inflate the inflatable balloon to the second side channel.*

*6. The radiating device according to claim 5 wherein the fluid used to inflate the inflatable balloon is a liquid.*

*7. The radiating device according to claim 5 wherein the fluid used to inflate the inflatable balloon is a gas.*

*8. The radiating device according to claim 2 wherein the fluid comprises a conditioning liquid.*

*9. The radiating device according to claim 2 wherein the fluid comprises a solution of a selective cytotoxicity substance.*

*10. The radiating device according to claim 2 wherein the antenna comprises a linear dipole antenna.*

*11. The radiating device according to claim 10 wherein the linear dipole antenna comprises a coil-shaped segment.*

*12. The radiating device according to claim 2 further comprising a stainless steel wire coupled to the at least one temperature sensing device.*

* * * * *